United States Patent [19]

Chang

[11] Patent Number: 4,877,744
[45] Date of Patent: Oct. 31, 1989

[54] QUALITATIVE METABOLISM ASSESSMENT USING HIGH PERFORMANCE THIN LAYER CHROMATOGRAPHY

[75] Inventor: Shih-Ling Chang, Lexington, Ky.

[73] Assignee: The University of Kentucky Research Foundation, Lexington, Ky.

[21] Appl. No.: 77,924

[22] Filed: Jul. 27, 1987

[51] Int. Cl.$^4$ .............................................. G01N 30/90
[52] U.S. Cl. ...................................... 436/162; 436/161
[58] Field of Search .................. 436/161, 162, 56, 57, 436/183, 804; 128/630; 422/68–71

[56] References Cited

U.S. PATENT DOCUMENTS 3,963,421  6/1976  Jones .................................... 436/162
4,741,830  5/1988  Hauck et al. ......................... 436/162

OTHER PUBLICATIONS

"Dextromethorphan is a Safe Probe for Debrisoquine Hydroxylation Polymorphism", Kupfer, A., Schmid, B., and Preisig, R., The Lancet:517–518, Sept. 1, 1984.

"Methoxyphenamine and Dextromethorphan as Safe Probes for Debrisoquine Hydroxylation of Polymorphism", Roy, S. D., Hawes, E. M., Hubbard, J. W., McKay, G., and Midha, K. K., The Lancet:1393, Dec. 15, 1984.

"Polymorphic Dextromethorphan Metabolism: Co-Segregation of Oxidated O-Demethylation with Debrisoquine Hydroxylation", Schmid, B., Bircher, J., Preisig, R., and Kupfer, A., Clin. Pharmacol. Ther. 38 (6):618–624 (1985).

"Interindividual differences in Dextromethorphan Kinetics in Man", De Zeeuw, R. A., Jonkman, J. H. G., and Cabana, B. E., Abstr. Acta Pharmacol. et Toxicol., III World Conference on Clin. Pharmacol. & Therapeut. Stockholm (Jul. 27–Aug. 1, 1986).

"Pharmacogenetics of Dextromethorphan O-Demethylation in Man", Kupfer, A., Schmid, B., and Pfaff, G., Xenobiotica, 16(5):421–433 (1986).

Dengler Von H. J., and Eichelbaum, M., Arzneim.-Forsch./Drug Res. 27(II), Nr. 9b:1836–1844 (1977).

"A Population and Familial Study of the Defective alicyclic Hydroxylation of Debrisoquine among Egyptians", Mahgoub, A., Idle, J. R., and Smith, R. L., Xenobiotica 9 (1):51–52 (1979).

"A Family and Population Study of the Genetic Polymorphism of Debrisoquine Oxidation in a White British Population", Price Evans, D. A., Mahgoub, A., Sloan, T. P., Idle, J. R., and Smith, R. L., J. Med. Genet. 17:102–103 (1980).

"Deficient Metabolism of Debrisoquine and Sparteine", Inaba T., Otton, S. V., and Kalow, W., Clin. Pharmacol. Ther. 27:547 (1980).

"The Genetic Control of Sparteine and Debrisoquine Metabolism in Man with New Methods of Analyzing Bimodal Distributions", Evans et al, J. Med. Genet. 20:321 (1983).

"Sparteine Oxidation Polymorphism in Denmark", Brosen, K., Otton, S. V. and Gram, L. F., Acta Pharmacol et toxicol 57:357–358 (1985).

"Pharmacogenetics of Mephenytoin; A New Drug Hydroxylation Polymorphism in man", Kupfer, A. and Preisig, R., Eur. J. Clin. Pharmacol 26:753–754 (1984).

"Relationship of N-demethylation of Amiflamine and its Metabolite to Debrisoquine Hydroxylation Polymorphism", Alvan et al, Clin. Pharmacol Therap 36(4):515–517 (1984).

"Nortriptyline and Debrisoquine Hydroxylations in Ghanaian and Swedish subjects", Woolhouse et al, Clin. Pharmacol Therap 36(3):374–375 (1984).

"Mephenytoin hydroxylation deficiency in Caucasians: frequency of a New Oxidative Drug Metabolism Polymorphism", Wedlund et al., Clin. Pharmacol. and Therapeut. 36(6):773–774 (1984).

"Metoprolol Metabolism and Debrisoquine Oxidation Polymorphism–Population and Family Studies", McGourty et al, Br. J. Clin. Pharmac. 20:555–557 (1985).

"Genetic Polymorphism of Mephenytoin p(4')-Hydroxylation: difference between Orientals and Caucasians", Jurima et al, Br. J. Clin. Pharmac. 19:483–484 (1985).

"A Family Study of Genetic and Environmental Factors determining Polymorphic Hydroxylation of Debrisoquin", Steiner et al., Clin. Pharmacol. Ther. 38:394–395 (1985).

"No Evidence for The Presence of Poor Metabolizers of Sparteine in An Amerindian Group; The Cunas of Panama", Arias, et al, Br. J. Clin. Pharmac. 21:547–548 (1986).

"Co-inheritance of the Polymorphic Metabolism of Encainide and Debrisoquine", Woosley et al., Clin. Pharmacol Ther 39(3):282–285 (1986).

"Debrisoquine Oxidation in An Australian Population", Peart et al., Br. J. Clin. Pharmac. 21:465–466 (1986).

"Determination of Dextromethorphan and Metabolites in Human Plasma and Urine by High-Performance Liquid Chromatography with Fluorescence Detection", East, T. And Dye, D., J. Chromat. 338:99–112 (1985).

"The Genetic Polymorphism of Sparteine Metabolism", Eichelbaum et al., Xenobiotica, 16(5):465–475 (1986).

"Quantitative Determination of Dextromethorphan and Three Metabolites in Urine by Reverse-Phase High-Performance Liquid Chromatography", Park et al, J. Pharmaceut. Sci. 73(1):24–29 (1984).

"Determination of Dextromethorphan in Biological Fluids by Liquid Chromatography by using Semi-Microbore Columns", Achari et al, J. Pharmaceut. Sci. 73(12):1821–1822 (1984).

*Primary Examiner*—Barry S. Richman
*Assistant Examiner*—T. J. Wallen
*Attorney, Agent, or Firm*—Lowe, Price, LeBlanc, Becker & Shur

[57] ABSTRACT

A method for the qualitative assessment of oxidative drug metabolism deficiencies, preferably for the qualitative assessment of dextromethorphan metabolism, in a subject comprises analyzing a sample fluid from the subject, for example urine, which contains metabolites of a probe drug using high performance thin layer chromatography.

8 Claims, No Drawings

QUALITATIVE METABOLISM ASSESSMENT USING HIGH PERFORMANCE THIN LAYER CHROMATOGRAPHY

FIELD OF THE INVENTION

The present invention relates to a method for the qualitative assessment of oxidative drug metabolism deficiencies in a subject. The subject may be human or a nonhuman animal. The present invention further relates to a method for the qualitative assessment of dextromethorphan metabolism in a subject.

BACKGROUND OF THE INVENTION

Interest in the pharmacogenetics of oxidative drug metabolism has grown rapidly in the past several years. It has been discovered that a genetic deficiency in oxidative drug metabolism exists in certain subjects which causes the subjects to act as a slow or poor metabolizer rather than a fast, efficient or extensive metabolizer of certain drugs. Several drugs have been used as probes for the assessment of oxidative drug metabolism deficiencies in subjects, including dextromethorphan, debrisoquine and sparteine. See, for example, Kupfer et al, "Dextromethorphan as a Safe Probe for Debrisoquine Hydroxylation Polymorphism", *The Lancet* (Sept. 1, 1984), pages 517-518; Roy et al, "Methoxyphenamine and Dextromethorphan as Safe Probes for Debrisoquine Hydroxylation Polyamorphism", *The Lancet* (Dec. 15, 1984), page 1393; Schmid et al, "Polymorphic Dextromethorphan Metabolism: Co-Segregation of Oxidative O-Demethylation with Debrisoquine Hydroxylation", *Clinical Pharmacology and Therapeutics*, Vol. 38, No. 6 (1985), pages 618-624; De Zeeuw et al, "Interindividual Differences in Dextromethorphan Kinetics in Man", *Acta Pharmacologica et Toxicologica*, Vol. 59, Supplement V (1986), page 44; and Kupfer et al, "Pharmacogenetics of Dextromethorphan O-Demethylation in Man", *Xenobiotica*, Vol. 16, No. 5 (1986), pages 421-433, for further details of previous studies in this regard.

Generally, pharmacogenetic screening using the aforementioned or other drugs as probes has been conducted by administering the probe drug to a subject and then quantitatively monitoring a body fluid containing metabolites of the probe drug. Known methods for analyzing body fluids such as urine containing the drug and its metabolites include gas chromatography and high performance liquid chromatography. Both gas chromatography and high performance liquid chromatography provide a quantitative indication of the relative amounts of the probe drug and the metabolites of the probe drug in the sampled body fluid. The gas chromatography and high performance liquid chromatography method are particularly suitable for determining the relative amounts of the substances. Reports of pharmacogenetic screenings using either gas chromatography or high performance liquid chromatography techniques are disclosed by, for example, Price Evans et al, *Journal of Medical Genetics*, 17 (1980), pages 102-105 (gas chromatography); Kupfer et al, *European Journal of Clinical Pharmacology*, 26 (1984,) pages 753-759 (gas liquid chromatograph); Wedlund et al, *Clinical Pharmacology and Therapeutics*, Vol. 36, No. 6 (1984), pages 773-780 (high performance liquid chromatography); Jurima et al, *British Journal of Clinical Pharmacology*, 19 (1985), pages 483-487 (gas chromatography); and Eichelbaum et al, *Xenobiotica*, Vol. 16, No. 5 (1986), pages 465-481 (gas chromatography).

Additionally, determinations of dextromethorphan and its metabolites using high pressure liquid chromatography suitable for use in pharmacogenetic screening procedures are disclosed by Park et al, *Journal of Pharmaceutical Sciences*, Vol. 73, No. 1 (1984), pages 24-29; Achari et al, *Journal of Pharmaceutical Sciences*, Vol. 73, No. 12 (1984), pages 1821-1822; and East et al, *Journal of Chromatography*, 338 (1985), pages 99-112.

While gas chromatography and high performance liquid chromatography are advantageous in providing quantitative analyses of oxidative drug metabolism during pharmacogenetic screening, these methods are disadvantageous in that they require complex, expensive equipment, including chromatographic columns, and in that they are time consuming. For example, in a typical arrangement, a high pressure liquid chromatography apparatus permits only one analysis per ten minute period. Thus, a need exists for a faster method of analysis in pharmacogenetic screening of oxidative drug metabolisms. A need also exists for such a method of analysis which uses more simple and inexpensive equipment than that required in the gas and high performance liquid chromatography techniques.

SUMMARY OF THE INVENTION

It is therefore an object of the present invention to provide a method for the assessment of oxidative drug metabolisms which is both more time efficient and inexpensive as compared with prior known methods. It is a more specific object of the present invention to provide a method for the assessment of oxidative drug metabolism deficiencies which is both time efficient and inexpensive.

It is a further object of the present invention to provide a method for the qualitative assessment of oxidative drug metabolism, particularly oxidative drug metabolism deficiencies, for use in time efficient and inexpensive pharmacogenetic screening procedures and phenotyping procedures. It is a further object of the present invention to provide a method for the qualitative assessment of dextromethorphan metabolism which may be performed both rapidly and economically.

These and additional objects are provided according to the present invention which generally comprises a method for the qualitative assessment of oxidative drug metabolism deficiencies in a subject. The method comprises analyzing a sample fluid from the subject, for example urine, which contains metabolites of a probe drug using high performance thin layer chromatography. A probe drug may be defined as a drug which is administered to a subject in a controlled amount in order to investigate metabolic characteristics of the subject with respect to the probe drug. High performance thin layer chromatography is classified under the general category of adsorption and/or partition chromatography and is generally known in the art. See, for example, *Practice of Thin Layer Chromatography*, Second Edition, J. C. Touchstone and M. F. Dobbins, John Wiley & Sons, Inc. New York, 1983, which is incorporated herein by reference. It has been discovered that by combining high performance thin layer chromatography with the use of probe drugs in determining oxidative drug metabolism deficiencies, a method is provided for the rapid, efficient and inexpensive qualitative assessment of oxidative drug metabolism deficiencies.

These and additional objects and advantages provided by the method of the present invention will become more fully understood in view of the following detailed description.

DETAILED DESCRIPTION

The present invention generally relates to a method for the qualitative assessment of oxidative drug metabolism deficiencies. The method allows for rapid, efficient and inexpensive phenotyping and pharmacogenetic screening of subjects. The method comprises analyzing a sample fluid from the subject which contains metabolites of a probe drug using high performance thin layer chromatography. The subject may be human or a nonhuman animal and suitably the sample fluid which is analyzed comprises urine.

As is known in the art, high performance thin layer chromatography is a specific type of adsorption and/or partition chromatography wherein the moving phase is liquid and the stationary phase is a solid adsorbing or partitioning material deposited on a flat supporting surface. The general procedures for high performance liquid chromatography are more fully described in *Practice of Thin Layer Chromatography*, Second Edition, cited above and incorporated herein by reference. Generally, the flat supporting surface comprises a glass plate although the flat plate may also be formed of materials such as ceramic or synthetic plastic materials including thermosetting and thermoplastic polymers. The adsorbent and/or partitioning material may comprise any of the conventional materials known in the art such as silica gel, alumina, diatomaceous earth, cellulose, reverse phase substances or mixtures thereof. Optionally, a binding agent, for example starch or the like, may be mixed with the adsorbent material to hold it in place on the flat plate. The adsorbent material is formed in a thin layer, for example having a thickness of 0.1 to 2.0 millimeters, on the flat plate.

A sample which is to be analyzed using high performance thin layer chromatography is generally mixed with a solvent and applied as a spot to the adsorbent surface of the plate. Thus, in accordance with the present invention, a sample fluid from the subject which contains metabolites of the probe drug, preferably urine, is mixed with a solvent and applied as a spot to the thin layer adsorbent surface deposited on the plate.

With the assistance of the high performance technique and capillary action, a solvent such as Davidow (composed of ethyl acetate 85 parts, methanol 10 parts and ammonium hydroxide 5 parts) or any other appropriate solvent systems known to the art for use in thin layer chromatography migrates up the thin layer of adsorbent material. Simultaneously, the various constituents of the sample fluid migrate along the adsorbent material to resolve the original spot of mixture into a series of spots corresponding to each or several components of the mixture. For example, any remainder of the probe drug and any of its different metabolites contained in the sample migrate along the adsorbent material to resolve the original spot of sample fluid into a series of spots corresponding to each probe component or several components, thereby separating the drug from its metabolites. The spots may be visualized by spraying them with a suitable color producing agents such as the known Dragendorff's reagent followed by 5% sodium nitrite spray or any other established visualization reagents known in the art for use with thin layer chromatography. According to the present invention, it has been discovered that the high performance thin layer chromatography is particularly suitable for resolving a sample of body fluid containing a probe drug and its various metabolites into a series of spots corresponding to each component thereby forming a chromatogram.

In a preferred method according to the present invention, the subject under study is administered a dosage of a probe drug. Thereafter, a body fluid of the subject which contains the metabolites of the probe drug, for example urine, is continuously collected, and the collected fluid is analyzed using high performance thin layer chromatography as discussed above. The high performance thin layer chromatography is particularly adapted for resolving the sample body fluid and separating the various metabolites contained therein from one another and from any unmetabolized probe drug. Moreover, once the resolved spots are visualized, visual observation of the thin layer plate will indicate a qualitative assessment of the subject's probe drug metabolism characteristics. Particularly, the chromatography will visually indicate whether there is a significantly greater amount of unmetabolized drug contained in the sample whereby the subject is a slow or poor oxidative drug metabolizer, or whether there is a relatively greater amount of the different metabolites contained in the sample whereby the subject is a fast or efficient oxidative drug metabolizer.

A more specific embodiment of the present invention comprises a method for the qualitative assessment of dextromethorphan metabolism in a subject. The method comprises analyzing a sample fluid from the subject which contains dextromethorphan metabolites using high performance thin layer chromatography as discussed above. Preferably, the subject is administerd a dosage of dextromethorphan, a body fluid of the subject which contains dextromethorphan metabolites, preferably urine, is continuously collected, and the collected body fluid is analyzed using high performance thin layer chromatography.

According to the method of the present invention, qualitative screening of patients for a deficiency in oxidative drug metabolism, for example the deficiency affecting dextromethorphan metabolism, may be performed rapidly and economically. Thus, such screenings can be performed prior to initiating therapy with drugs influenced by the oxidative drug metabolism deficiencies. The following example demonstrates the suitability of the method of the present invention for qualitative screening of patients.

EXAMPLE

This example demonstrates the method of the present invention using human subjects. A control urine sample was taken from each of twelve subjects prior to beginning the testing procedure. Each subject then ingested 60mg of dextromethorphan, and complete urine collection was performed for 8 hours after drug administration. Each urine same, including the control samples, was analyzed using high performance thin layer chromatography. Specifically, following urine hydrolysis and extraction, samples were dissolved in dichloromethane and spotted on a 10 cm high performance thin layer chromatography silica gel plate. The plate was placed in a sealed glass tank containing the mobile phase solvent (composed of ethylacetate 85 parts: methanol 10 parts and ammonium hydroxide 5 parts) and developed vertically for 5 cm. The plate was removed from the tank, dried and then sprayed with Ludy Tenger reagent (containing 5 gm bismuth subcarbonate +15 ml hydrochloric acid +15 gm of potassium iodide and 85 ml of water) followed by a 5% sodium nitrite spray. For comparison, all samples were also analyzed using high performance liquid chromatography methods. Qualitative examination of the chromatograms resulting from the high pressure thin layer chromatography clearly distinguished 10 efficient or fast metabolizer phenotypes and 2 slow or poor metabolizer phenotypes in the group. No interfering substances were detected in any of the control urine samples. For confirmation, according to the high performance liquid chromatography method, dextromethorphan and two of its metabolites, dextrorphan and (+)-3-morphinanol were quantified in each urine sample using fluorescence detection. The ratios between dextromethorphan and the dextrorphan metabolite ranged between 0.02 and 0.05 for 10 of the subjects, i.e., the fast or efficient metabolizers indicated in the high pressure thin layer chromatography results. The ratio of dextromethorphan and the dextrorphan metabolite for the remaining 2 subjects were 7.5 and 16.2, thus confirming the qualitative indication of the 2 slow or poor metabolizer noted from the high performance thin layer chromatography results. As with the high pressure thin layer chromatography method, no interfacing substances were detected in any of the control urines by the high performance liquid chromatography method. Thus, the method according to the present invention provides a rapid, efficient and economical means for qualitatively screening patients for deficiencies in oxidative drug metabolism, particularly dextromethorphan metabolism.

The preceding Example is set forth to illustrate a specific embodiment of the invention and is not intended to limit the scope of the methods of the present invention. Additional embodiments and advantages within the scope of the claimed invention will be apparent to one of ordinary skill in the art.

What is claimed is:

1. In a method for characterizing the oxidative phenotype of a subject comprising collecting a fluid sample from the subject, analyzing the sample to quantitatively determine the presence of oxidative metabolites of a drug and comparing the results obtained for the subject with those obtained for a normal subject subsequent to the administration of said drug, the improvement wherein the analyzing step is rapidly conducted by high performance thin layer chromatography to qualitatively assess the metabolite pattern of the subject; and the comparing step is conducted by visually comparing the subject's metabolite pattern to a normal subject's metabolite pattern.

2. The method of claim 1, wherein
the drug is dextramethorfan; and
the sample is urine.

3. The method of claim 1, wherein
the thin layer chromatography is performed on an adsorbent layer of a material selected from the group consisting of silica gel, alumina, diatomaceous earth, cellulose, and mixtures thereof on a flat plate formed of a material selected from the group consisting of glass, ceramic, and synthetic plastic materials.

4. The method of claim 1, wherein the collecting, analyzing and comparing steps are repeated at a specified time interval.

5. In a method for characterizing the oxidative phenotype of a subject comprising administering to the subject an amount of a probe drug effective to yield detectable amounts of the drug and its oxidative metabolites in a fluid sample of the subject taken at a specified time subsequent to the administration of the drug, collecting a fluid sample from the subject, analyzing the fluid sample to quantitatively determine the exact ratio of drug to metabolites present in the sample and comparing the subject's ratio to a normal oxidative ratio, the improvement wherein the analyzing step is rapidly conducted by high performance thin layer chromatography to qualitatively assess the metabolite, pattern of the subject; and the comparing step is conducted by visually comparing the subject's pattern to a normal subject's metabolite pattern.

6. The method of claim 5, wherein
the drug is dextramethorfan; and
the sample is urine.

7. The method of claim 5, wherein
the thin layer chromatography is performed on an adsorbent layer of a material selected from the group consisting of silica gel, alumina, diatomaceous earth, cellulose, and mixtures thereof on a flat plate formed of a material selected from the group consisting of glass, ceramic, and synthetic plastic materials.

8. The method of claim 5, wherein
the collecting, analyzing and comparing steps are repeated at a specified time interval.

* * * * *